United States Patent
Stachowski et al.

(10) Patent No.: US 8,342,467 B2
(45) Date of Patent: Jan. 1, 2013

(54) APPARATUS FOR HAND CONTROL, PRESSURE AMPLIFICATION, AND STABILIZATION OF MEDICAL AND INDUSTRIAL DEVICES

(76) Inventors: Eric Ronald Stachowski, Sebastopol, CA (US); Garrett W Brown, Philadelphia, PA (US)

(*) Notice: Subject to any disclaimer, the term of this patent is extended or adjusted under 35 U.S.C. 154(b) by 332 days.

(21) Appl. No.: 11/538,298

(22) Filed: Oct. 3, 2006

(65) Prior Publication Data

US 2007/0080275 A1 Apr. 12, 2007

Related U.S. Application Data

(60) Provisional application No. 60/596,573, filed on Oct. 4, 2005.

(51) Int. Cl.
*E04G 3/00* (2006.01)
(52) U.S. Cl. ............ 248/280.11; 248/281.11; 248/284.1
(58) Field of Classification Search ............ 248/123.11, 248/325, 280.11, 292.11, 584, 281.11, 284.1, 248/276.1, 591; 352/243; 224/185; 396/420, 396/421
See application file for complete search history.

(56) References Cited

U.S. PATENT DOCUMENTS

| | | | |
|---|---|---|---|
| 4,208,028 A | 6/1980 | Brown | |
| 4,394,075 A | 7/1983 | Brown | |
| 4,523,732 A * | 6/1985 | Biber et al. | 248/123.11 |
| 4,682,749 A * | 7/1987 | Strater | 248/284.1 |
| 5,213,293 A * | 5/1993 | Muentener et al. | 248/123.11 |
| 5,360,196 A | 11/1994 | DiGiulio | |
| 5,435,515 A | 7/1995 | DiGiulio | |
| 5,579,071 A | 11/1996 | Wetzel | |
| 5,738,316 A * | 4/1998 | Sweere et al. | 248/123.11 |
| 5,842,672 A * | 12/1998 | Sweere et al. | 248/278.1 |
| 5,918,841 A * | 7/1999 | Sweere et al. | 248/123.11 |
| 6,012,693 A * | 1/2000 | Voeller et al. | 248/280.11 |
| 6,419,196 B1 * | 7/2002 | Sweere et al. | 248/276.1 |
| 6,523,796 B2 * | 2/2003 | Abramowsky et al. | 248/284.1 |
| 6,575,644 B2 * | 6/2003 | Paddock et al. | 396/421 |
| 6,592,090 B1 * | 7/2003 | Li | 248/284.1 |
| 7,014,157 B2 * | 3/2006 | Oddsen | 248/280.11 |
| 7,255,311 B2 * | 8/2007 | Metelski | 248/123.11 |
| 7,618,016 B2 * | 11/2009 | Brown | 248/584 |
| 8,066,251 B2 * | 11/2011 | Brown | 248/584 |
| 2005/0224664 A1 * | 10/2005 | Metelski | 248/123.11 |
| 2006/0263082 A1 * | 11/2006 | Brown | 396/421 |

* cited by examiner

*Primary Examiner* — Bradley Duckworth
(74) *Attorney, Agent, or Firm* — Steven A. Nielsen; Allman & Nielsen, P.C.

(57) ABSTRACT

An equipoising arm structure that can selectively exert force in any direction—lifting, pressing down, or applying lateral bias—with consistent force throughout its range of articulation, comprises a force exerting device having a force exerting structure including a load arm as a first side pivotable about a load pivot, a resilient member attached to the load arm and to a termination point and forming a second side of the force exerting structure. The third side of the structure is formed by a line from the termination point to the load pivot. A first adjustment mechanism moves the termination point to change the length and disposition of the third side of the structure to positions above or below the load pivot. Additional adjustment mechanisms may alter the mounting angle of the entire force exerting structure, and/or the angular relationship between a plurality its force-exerting component devices.

8 Claims, 8 Drawing Sheets

APPARATUS FOR HAND CONTROL, PRESSURE AMPLIFICATION, AND STABILIZATION OF MEDICAL AND INDUSTRIAL DEVICES

CROSS-REFERENCES TO RELATED APPLICATIONS

The application claims the benefit of U.S. provisional application 60/596573 filed on Oct. 4, 2005 which is incorporated herein by reference.

STATEMENT REGARDING FEDERALLY SPONSORED RESEARCH OR DEVELOPMENT

Not Applicable.

REFERENCE TO A SEQUENCE LISTING

Not Applicable.

BACKGROUND OF THE INVENTION

1. Field of the Invention

The present invention relates to an apparatus for reducing the effort and force required to place and hold a medical instrument on or against a patient. The present invention may be used in performing ultrasound examinations. The present invention includes an equipoising arm structure that can selectively exert force in any direction—lifting, pressing down, or applying lateral bias—with consistent force throughout its range of articulation.

2. Background of the Present Invention

The placement of a medical device on or against the skin of a patient typically requires physical exertion by the operator or medical practitioner. Such medical devices have their own weight and are often attached to cumbersome wires or tubes. Medical practitioners face further physical challenge due to the need to firmly press the medical device against the skin of a patient for extended periods of time.

Ultrasound examinations require direct skin contact with a medical instrument and the application of steady force against the skin of a patient. Different patients require different directions and magnitudes of applied force during an ultrasound examination. For example, a prone pregnant woman or obese patient will require the mild application of downward and lateral pressure to fully cover the abdominal area. On the other hand, a shoulder examination for a patient sitting upright may require firm side pressure or pressure perpendicular to the Earth's gravity.

Many medical devices, such as transducers used in ultrasound examinations, are coated in a jelly type material and are then pressed against the skin of a patient. With the use of such jelly, the patient's skin presents a slippery, moving, and sometimes squirming surface. The medical practitioner is then faced with the physical challenge of pressing and systematically moving the medical device on a three dimensional surface that is slippery, moving, and breathing.

Many medical practitioners experience muscle fatigue and injury as a result of the physical exertion required in performing ultrasound examinations or similar examinations with other medical devices. Thus, there is an urgent need in the art for means to reduce the physical effort expended by medical practitioners in performing ultrasound examinations or similar procedures.

Robotic arms are known in the related art and are used in many industries to perform automated tasks or to reduce human physical effort. Most medical procedures do not lend themselves to the use of typical industrial robots or mechanical arms. Most medical procedures require a skilled, delicate, human directed touch to be effective and to be accepted by patients. For example, a pregnant woman might only reluctantly consent to an ultrasound examination performed with a large or computer controlled robotic arm.

There is a need in the art for means to allow hand placement and hand controlled pressure of medical devices on or against patients while reducing muscle fatigue and injury to medical practitioners. There is a need in the art for non-obtrusive means to amplify the force used by medical practitioners in manipulating medical devices.

Spring powered 'equipoising' parallelogram arms have been used for decades to support and position medical payloads such as x-ray machines and dental equipment. These arms rely to a greater or lesser extent on friction to retain a set angle or position, since existing spring geometries do not necessarily provide appropriate or consistent lift throughout the entire angular excursion of the parallelogram links. The invention of the articulated, force-exerting arms marketed under the trademark Steadicam®, however, has provided nearly frictionless support of a floating camera payloads in order to isolate them from unwanted spatial movements of camera operators, employing a spring design for the support arm that 'equipoises' the payload, countering the fixed weight of the gimbaled camera assembly with nearly constant positive buoyancy from its lowest to its highest point of parallelogram articulation.

The formulas for determining the appropriate spring rate to achieve equipoise factor down to the expression K=P/d, where K is the spring rate, P is the load and d is the height of the lifting triangle which is incorporated into the parallelogram and exercises it upward. When a spring of the rate specified in the above formula is deployed as the third side of the triangle, it produces the appropriate force to exactly lift the specified weight throughout the entire vertical range of articulation. This property is termed "iso-elasticity".

U.S. Pat. No. 5,360,196 and continuation U.S. Pat. No. 5,435,515 (incorporated herein by reference), disclose adjusting the lifting strength of the arm in a novel manner by raising and lowering the effective spring attachment point along a path angularly offset from the adjacent vertical link of the parallelogram (thus increasing or decreasing the height and also the efficiency of the lifting triangle) without compromising the spring rate required to provide 'iso-elasticity'. The same formula, K=P/d, indicates that if the height of the appropriate lifting triangle is increased or reduced proportionately with the weight to be carried, the property of iso-elasticity will be maintained.

However, there is a need in the art for means to push down and/or laterally rather than just lift up, in order to reduce the physical effort exerted by medical professionals in performing ultrasound examinations and still maintain the "hands on" skill and patient comfort provided by a human being.

SUMMARY OF THE INVENTION

The present invention is directed to the field of equipoising force-exerting arms for hand control, pressure amplification and stabilization of medical and industrial devices.

Illustrative embodiments of the invention comprise tensioning assemblies that can provide separate, continuous adjustments of both the magnitude and the vector of exerted force.

A first adjustment can alter the geometric relationship between the end point of the tensioning assembly and the remaining structures that comprise the support arm, in order to provide an adjustable exerted force in relation to the vector of gravity that is consistent throughout the articulation of the support arm.

A second, optional adjustment can alter the angle of the fixed support for the entire arm assembly in order to redirect the force resulting from the first adjustment in vectors non-parallel to that of gravity.

A third, optional adjustment can bias the individual hinge segments that interconnect the various sections of the arm assembly in order to selectably add a separate, and/or additional, lateral force.

In a first, separate, aspect of an illustrative embodiment of the invention, a force-exerting triangle, which provides the lifting or pressing-down power for the support arm, comprises a load arm pivotable about a load pivot and forming a first side of a force exerting structure; a resilient member having a first end attached to the load arm and a second end attached to a termination point displaced from the load pivot and forming a second side of the force exerting structure; a force exerting structure third side extending from the termination point to the load pivot; and an adjustment mechanism to move the termination point to change the length of the third side of the force exerting structure and/or its spatial disposition with respect to the load pivot, for the purpose of exerting the desired magnitude and vector of force. As the long first side articulates about the pivot with the short third side, the consistency of exerted power can be regulated by fixing the short side of the lifting triangle at a nominal offset angle with reference to vertical. In addition, the vector of the exerted force can either oppose or augment the force of gravity as the third side of the triangle is adjustably disposed above or below the pivot with the long side.

Embodiments of the invention are directed to a force-exerting triangle operating in conjunction with a parallelogram support arm and comprising a substantially vertical shorter side, a longer side and another side that consists of a flexible, resilient member, the expansion or contraction of which pivotally biases the apex angle of the sides (and thus the associated parallelogram) from its most obtuse form, up past the condition of being a right angle and on up to its most acute form.

The long side of the lifting triangle can be contiguous with one of, or parallel to, the long articulating sides of the parallelogram.

The angle of the short side is variably fixed in angular reference to the adjacent, roughly vertical, short leg of the parallelogram (with reference to a plumb line that passes through the apex of the triangle), such that the degree of iso-elasticity can remain nominally acceptable, even if the selected spring rate of the resilient member does not conform to the K=P/d formula for iso-elasticity. The length of the short side (and its disposition either above or below the long articulating side) can be continuously adjusted, thus providing for force exertion that varies infinitely between opposing or augmenting gravity. This provides a unique, adjustable, mechanism capable of 'pressing-down' on demand—as much or as little as required.

Embodiments of the invention provide the features described in the four paragraphs immediately above by including a support arm for holding and manipulating a medical or industrial device that comprises a parallelogram linkage that is biased upwardly or downwardly by an extendable and retractable resilient member, one end of which may be selectably raised or lowered along a member mounted with respect to a pivot that is in fixed relationship to at least one side of the parallelogram.

In addition other exemplary embodiments of the invention are directed to a series of interconnected, force-exerting triangles, each associated with parallelogram support arms; the last of which is attached to the medical or industrial payload; the first of which is optionally mounted at an adjustably non-vertical angle, resulting in vectors of force that are non-parallel with that of gravity, and which, in combination, can therefore additionally exert 'pressing' force at any desired angle, including straight sideways.

It is noted that any shaped lifting structure can be used that follows the principals described herein and can be substituted for the "lifting triangle" referenced throughout. It is also noted that reference to a triangle or structure "sides" does not necessarily mean the sides are physical structures.

The present invention thereby provides means and methods to reduce the physical strain currently experienced by medical practitioners who perform ultrasound examinations and similar medical procedures. The present invention may be used to assist in such medical procedures and/or assist in the performance of tasks found in industrial environments.

The present invention overcomes the shortfalls in the related art by reducing the physical strain experienced by medical practitioners, using means that maintain the hands-on skill, touch, and emotional support provided by a medical practitioner. Unlike computer-controlled robotic arms, the payload, such as a transducer, of the present invention is directly guided by the hands of the medical practitioner, which preserves the ability to make micro fine adjustments in applied pressure based upon objective and subjective information obtained contemporaneously from the patient.

The present invention overcomes problems in the related art by reducing the physical strain currently experienced by medical practitioners by means that are not perceived by patients as threatening or impersonal.

The present invention overcomes problems in the related art by not requiring significant retraining of medical practitioners. The set-up, use, and maintenance of the robotic arms in the related art require a different skill set than the current skills of medical practitioners. The present invention attaches seamlessly to current medical devices and functions intuitively, requiring minimal retraining of medical practitioners.

The present invention overcomes shortfalls in the related art, which require the construction and use of new therapy heads to enclose ultrasound transducers or other medical devices. The present invention does not require the use of a therapy head as conventional medical devices may be attached directly to the present invention.

The present invention is suitable for use with a myriad of current medical devices and includes a universal transducer mount suitable for holding an ultrasound transducer, A-line transducer, or other medical device. The present invention does not require the fabrication of new medical devices or new ultrasound transducers since the disclosed universal mount has means to attach current medical devices to the disclosed apparatus.

The present invention provides a means of control wherein an equipoising and stabilizing arm adjustably produces mechanical force that amplifies and steadies the force applied by a medical practitioner to the ultrasound transducer or medical device in any useful vector.

BRIEF DESCRIPTION OF THE DRAWINGS

For further detail regarding embodiments of the force-exerting arms produced in accordance with the present invention, reference is made to the detailed description which is provided below, taken in conjunction with the following illustrations. The symbol "M" is sometimes used in the drawings to label a motor sometimes used to turn a lead screw.

DETAILED DESCRIPTION OF THE PREFERRED EMBODIMENTS

| Definition List 1 | |
|---|---|
| Term | Definition |
| articulating, force-exerting arm | An apparatus comprising parallelogram links and resilient means such as disclosed in U.S. Pat. Nos., 4,208,028 and 4,394,075 and 5,360,196 and continuation 5,435,515 |
| ultrasonographer | One who places a transducer on or against the skin of a patient. |
| lateral pressure | Pressure applied laterally to the side of a patient in vectors displaced as much as 90 degrees from that of gravity. |
| down pressure | Pressure applied toward the floor. |
| medical device | Any medical instrument such as an ultrasound transducer or therapy transducer that is positioned on or against a patient. |
| therapy head | A housing structure used by the related art to contain a medical device. |
| transducer | An ultrasound transducer used for either diagnosis or therapy. |

Currently, a transducer is manipulated upon a patient without mechanical assistance. Many medical devices require firm, but careful pressure to the skin of a patient. An example of such a medical device is a diagnostic ultrasound transducer used to provide imaging of the underlying tissue, organs or vessels. The use of such a transducer may require the application of a jelly type substance to the transducer and/or patient. In the past, medical practitioners, or ultrasonographers, experienced muscle fatigue and/or other injuries due to the intense physical requirements of firmly and steadily placing the transducer against the slippery skin of a patient for extended periods of time. Such injuries included strain and/or fatigue to the hand, arm and shoulder muscle groups, making the ultrasonographer's work experience painful, difficult and sometimes impossible.

The disclosed invention solves problems in the related art by associating this novel force-exerting triangle with a unique articulated parallelogram arm structure that can be adjusted to exert force in any direction relative to the vector of gravity. The disclosed invention is suitable for use with any medical device that is applied to the skin of a patient and is not limited to ultrasound equipment. The disclosed invention is also suitable for use in invasive procedures, where repetitive or strenuous movement is required by a medical practitioner, including liposuction procedures, or those in which medical instrument weight support is required such as arthroscopic surgery.

Figure 1:
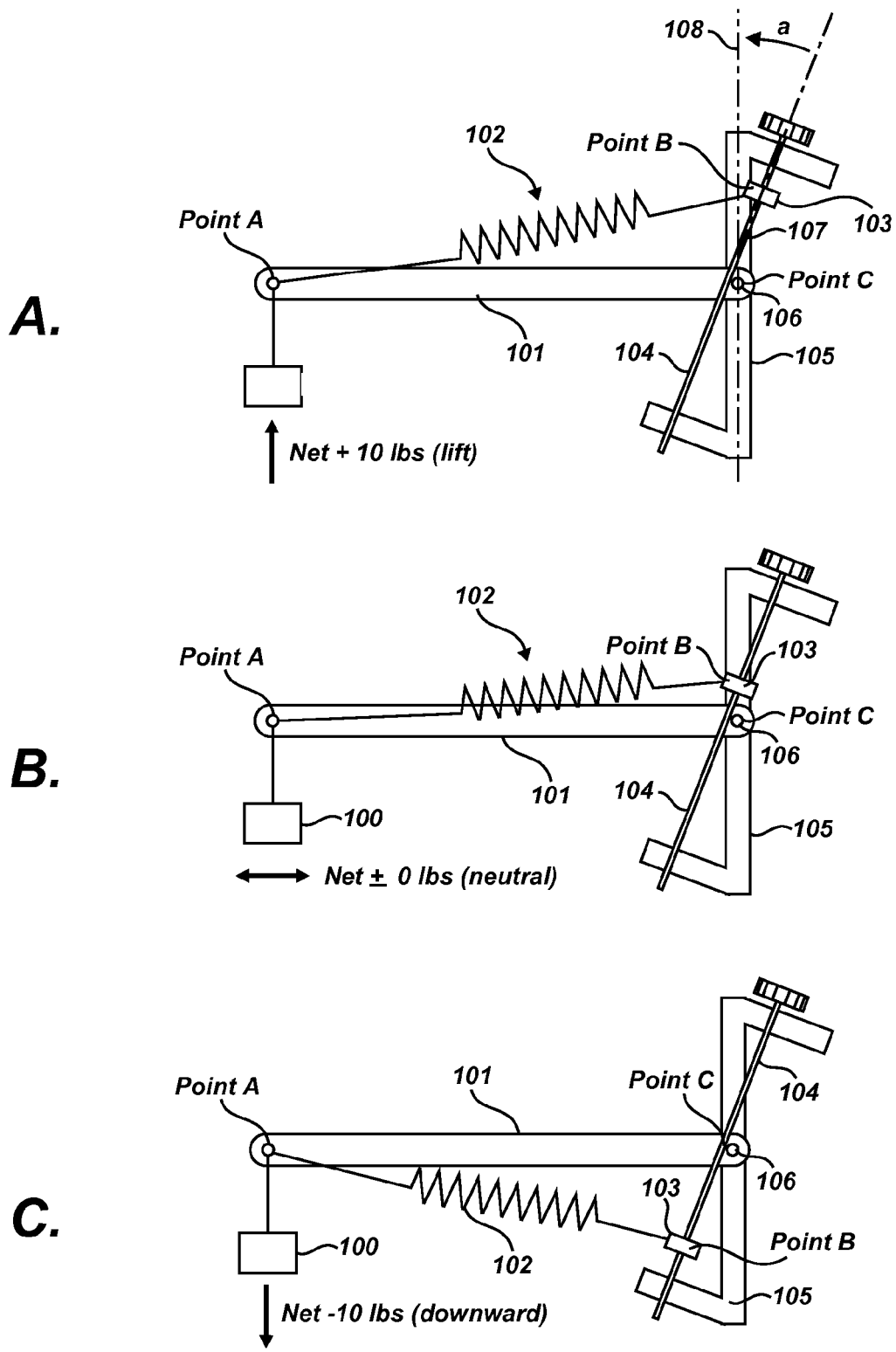
FIG. 1 provides three diagrammatic views of selected relationships between three force-exerting triangles and their associated payloads—illustrating, respectively, net lifting force, neutral force and gravity-augmenting down force produced by adjustment up or down of the tensioning means termination point.

FIG. 1 Provides three diagrammatic examples A, B and C of selected relationships between three force-exerting triangles, defined as points A, B, C and their associated payloads. In each example load arm 101 pivots about load pivot 106, biased by resilient tensioning means 102 to support payload 100. Examples A, B and C illustrate, respectively, net lifting force, neutral force and gravity-augmenting down force produced by adjustment up or down of the tensioning means 102 and its termination point B by means of carrier nut 103 driven up and down along lead screw 104 held by fixed end block 105. The successively descending positions of termination point B in these examples cause support arm 101 and payload 100 to be, respectively, urged upward by lift in example A, neutralized with respect to gravity in example B, and urged downward in example C. The values stated in pounds are not actual and are only for the purpose of illustration. In example A, angle a represents the deliberate, fixed displacement of the lead screw 104 from the vertical, so that the path of possible termination points of resilient means 102 crosses plumb line 108 that passes through load pivot 106. The crossing point 107 represents the BC distance that would uniquely provide iso-elastic articulation of load arm 101 about load pivot 106 to consistently lift (or push down) given payload 100 according to the formula K=P/d, where K=the spring rate of resilient flexible means 102, P=the amount of payload 100 and d =the distance BC (expressed positively or negatively) termination point B is displaced from load pivot 106.

Figure 2:
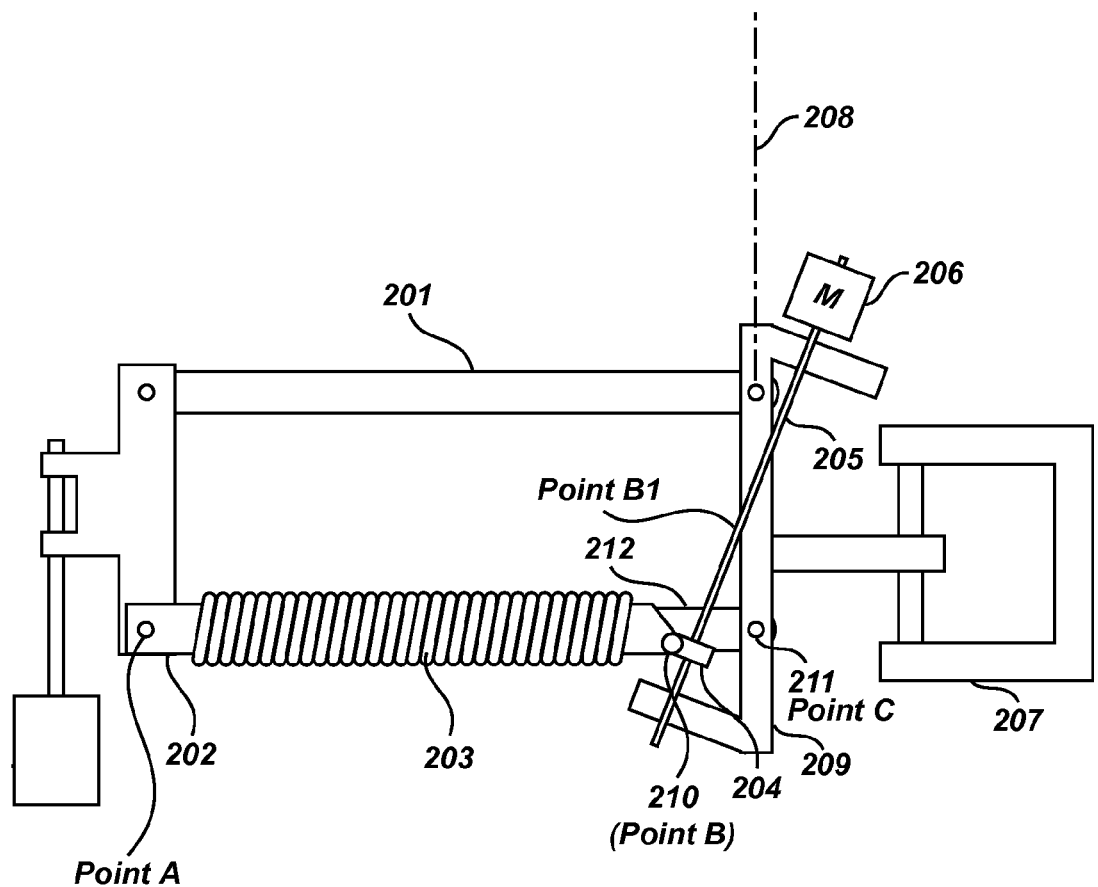
FIG. 2 is a perspective view of servo-controlled, motorized adjustment means to raise and lower the spring-termination point along a path offset from vertical and capable of descending below and/or outside the articulated parallelogram arm structure.

FIG. 2 depicts detail of an exemplary embodiment showing a first servo-controlled, motorized adjustment means 206 employed to raise and lower the spring-termination point 210 of lifting triangle ABC along path 205 offset from vertical 208, which path continues below and outside the articulated parallelogram arm structure 201. This adjustment can alter the geometric relationship between the end point of the tensioning assembly (210) and the remaining structures that comprise the support arm, in order to provide an adjustable exerted force in relation to the vector of gravity that is consistent throughout the articulation of the support arm.

In this embodiment, load arm 212 of the present invention is biased about load pivot 211 or point C, by lead screw 205 to raise and lower carrier nut 204 and thus attached termination point 210, or point B of spring 203, driven by an electric motor 206, to selectively alter the exact degree of downward pressure manifest at payload 200. Lead screw 205 is mounted fixedly to end block 209, which is angularly immobilized by mounting bracket 207. As illustrated, the lifting triangle ABC would yield a negative value for the third side BC which would strongly press down payload 200.

Point B1 illustrates the hypothetical spring termination along position along lead screw 205 at which the net load, including the weight of parallelogram 201 and payload 200, could be neutralized by a sufficiently positive value for the displacement B1 C of spring termination point 210, thus biasing the net load upward just enough to counter the downward force of gravity.

The illustrated termination point 210 or point B is on termination path or lead screw 205, displaced from vertical 208, shown below load pivot 211. If the appropriate values (the spring rate K of elastic, flexible, resilient means 203, the displacement distance d of the spring termination BC and the amount P of load 200) are consistent with the formula K=P/d as in FIG. 1, example C, the angular articulation of load arm 212 about load pivot 211 should yield consistent down force, termed "iso-elasticity", throughout its excursion.

Figure 3:
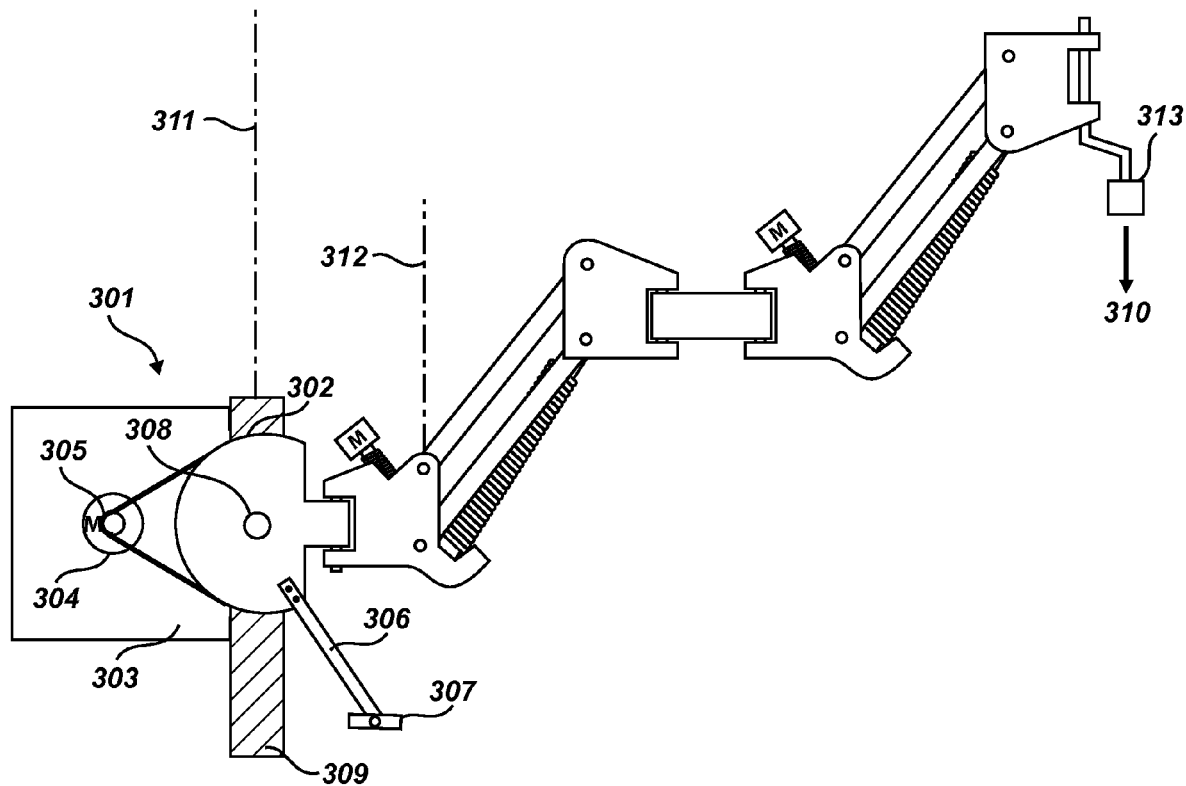
FIG. 3 is a perspective view of a double-articulated embodiment of a force-exerting arm, including a motorized connection assembly, pivotally associated with a mounting post, for adjustably redirecting the net arm force to a vector non-parallel with that of gravity.

FIG. 3 illustrates a second adjustment means that can alter the angle of the fixed support for the entire arm assembly in order to redirect the force resulting from the first adjustment (as above in FIG. 2) in vectors non-parallel to that of gravity. FIG. 3 depicts a double-articulated embodiment of a force-exerting arm 300, including a motorized, pivoting, single-axis connection assembly 301, pivotally associated with a mounting post 309, for adjustably redirecting the net exerted force 310 of the arm by causing axis 312 to be non-parallel with the direction of the force of gravity 311. Axis 312 of parallelogram arm assembly 300 is fixed in angular relationship with partial sector gear 302 which may pivot about axle 308 and driven by lever 306 with associated foot plate 307 or servo-driven by motor 304 via gear belt 303 and motor gear 305 to adjust the angle of axis 312 relative to vertical. Alteration of axis 312 correspondingly redirects the net vector of force 310 exerted by parallelogram arm assembly 300 as manifest at payload 313. Note that an additional axis of adjustment (not shown) roughly perpendicular to axle 308 is also contemplated, employing additional equipment of similar nature to connection assembly 301, or any equivalent gears, pivots, worm wheels, and the like known in the art capable of providing either manual or motorized redirection of net force vector 310 on any desired axis including those non-parallel with that of gravity.

Figure 4:
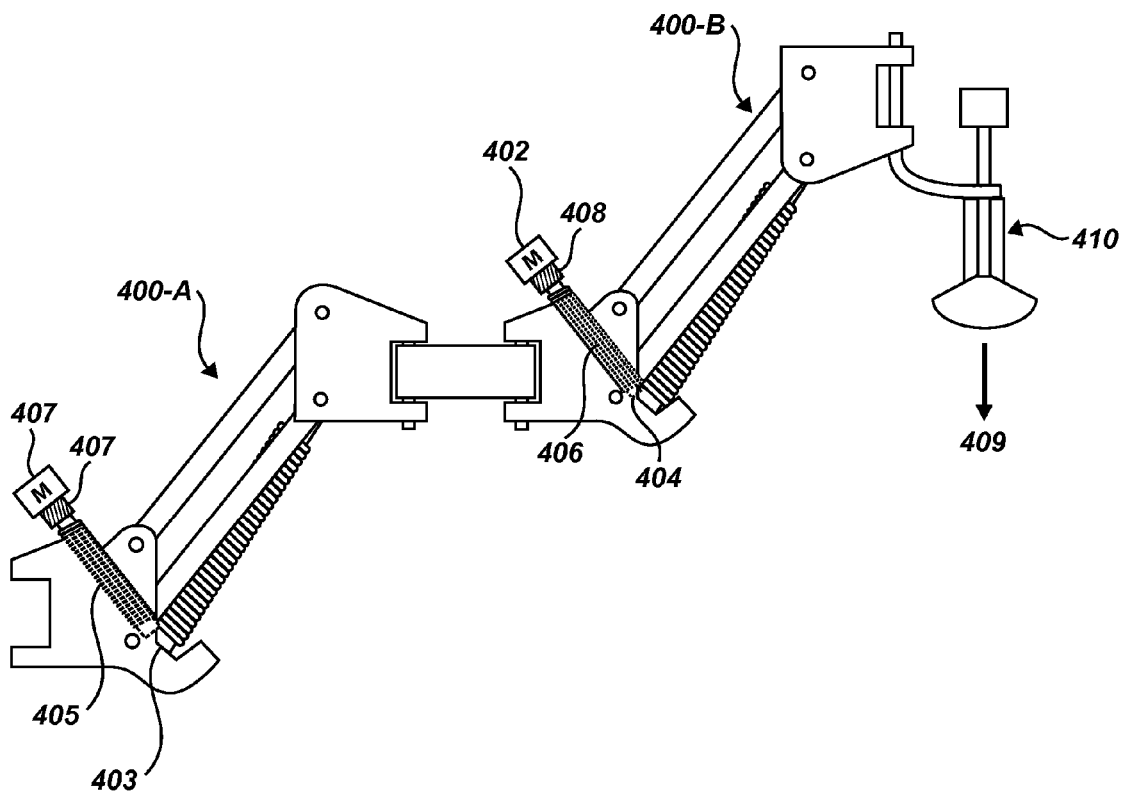
FIG. 4 is a perspective view of an articulating, force-exerting two-section embodiment of the arm of the present invention, equipped with electric motors to synchronously adjust the arms net force with respect to gravity—either 'upwardly' or 'downwardly'.

FIG. 4 depicts side view or sectional view of a two-section arm 400 of the present invention, equipped with electric motors (sometimes marked as "M") 401, 402 to synchronously adjust the arms net force 409 with respect to gravity—either 'upwardly' or 'downwardly'—as desired. Servo-operated motors 401, 402 with gear boxes 407, 408, drive lead screws 405, 406 roughly synchronously to bias spring termination carrier nuts 403, 404 along the paths of potential spring termination contiguous with lead screws 405,406. Note that termination point 403 will always be higher than termination point 404 because parallelogram arm 400A is required to lift parallelogram arm 400B in addition to payload 410, so the synchronicity of motor 401 with motor 402 will always be appropriately contoured. Servo control of synchronous motors 401, 402 can be by foot pedal (not shown) or by signals generated by force sensors associated with payload 410 (not shown).

Figure 5:
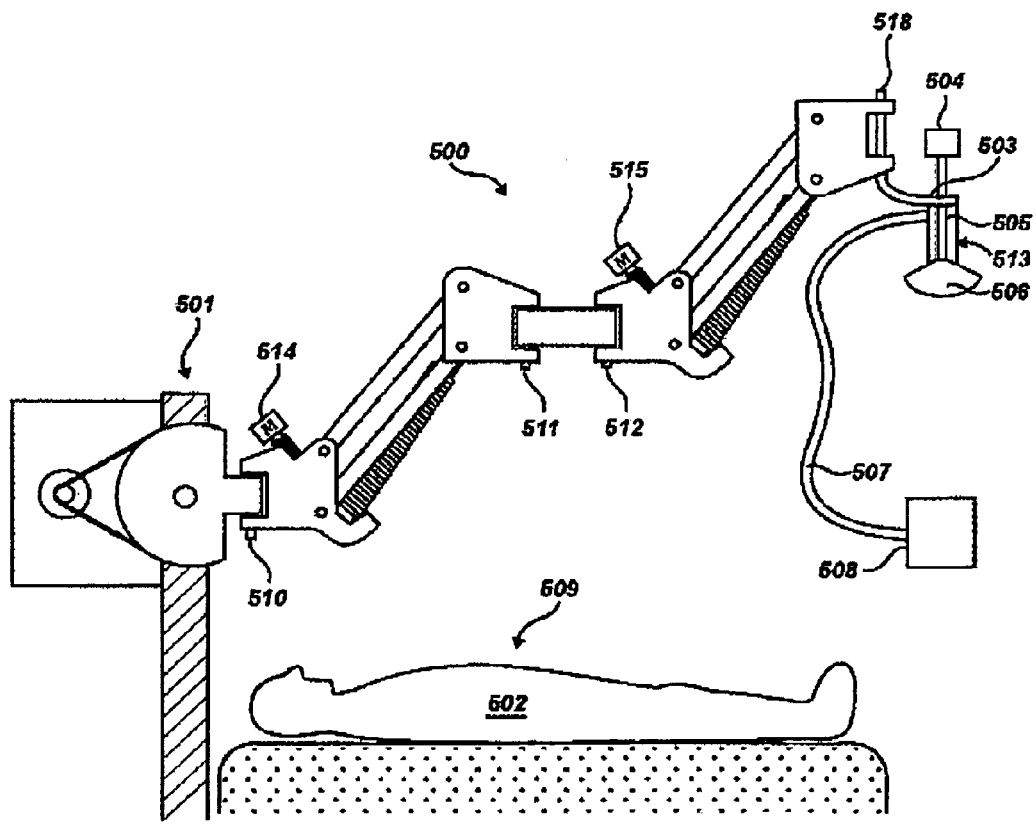
FIG. 5 shows an embodiment of the force-exerting arm of the present invention mounted adjustably to a solid bed post type mounting structure and attached to a payload (consisting of) comprising a universal transducer 'boot'-style mount and transducer.

FIG. 5 is the preferred embodiment, which shows the two section force-exerting parallelograms 500 of the present invention mounted adjustably to a solid bed post type mounting structure 501, which may be associated with a bed 502, and including a gimbaled attachment 503 to a universal transducer mount comprising a neoprene boot 505 plus transducer 506. The conventional, three-axis gimbal mount 503 (of conventional design) includes counterweight 504 so that the transducer is counterbalanced to be effortlessly poised at any angle. Electrical cord 507 is attached to the transducer and its opposite end is attached to ultrasound machine 508. In practice, cord 507 would be led along arm 500 in order not to interfere. In operation, the ultrasonographer may grasp neoprene boot 505 and angularly position transducer 506 appropriately by means of gimbal 503 in order to contact patient 509 with the desired vector and amount of exerted force. Nominally vertical hinges with axle pins 510, 511, 512 permit virtually effortless lateral motion of the interconnected arm segments and payload 513, unless pivoting mounting assembly 518 has caused hinge pins 510, 511, 512 to be disposed at an angle other than vertical, in which case the entire arm assembly 500 would tend to fall toward that angle and provide an increasing lateral vector of force as the displaced hinge pin angle further departs from vertical. Electric motors 514 and 515 may turn their respective lead screws.

The invention also includes a method of exerting downward and lateral forces on objects. A force-exerting device such as described herein is provided. The termination point is adjusted, preferably by servo-motorized means, to alter the length of the third side of the force-exerting triangle to change the lifting power of the force exerting triangle from positive to negative with respect to the vector of gravity. The mounting angle of the entire force-exerting device is additionally altered, either by manual lever means, or by servo-motorized means, to redirect the exerted force to vectors non-parallel with that of gravity. And the plurality of nominally vertical hinges interconnecting the various components of force-exerting device and its mounting means are pivotally biased around the respective hinge axes, preferably by servo-operated torque motors, to additionally alter the vector of the net exerted force so that the sum of the above methods permits medical and industrial practitioners to exert precisely directed forces in any direction with a minimum of sustained human effort.

Figure 6:
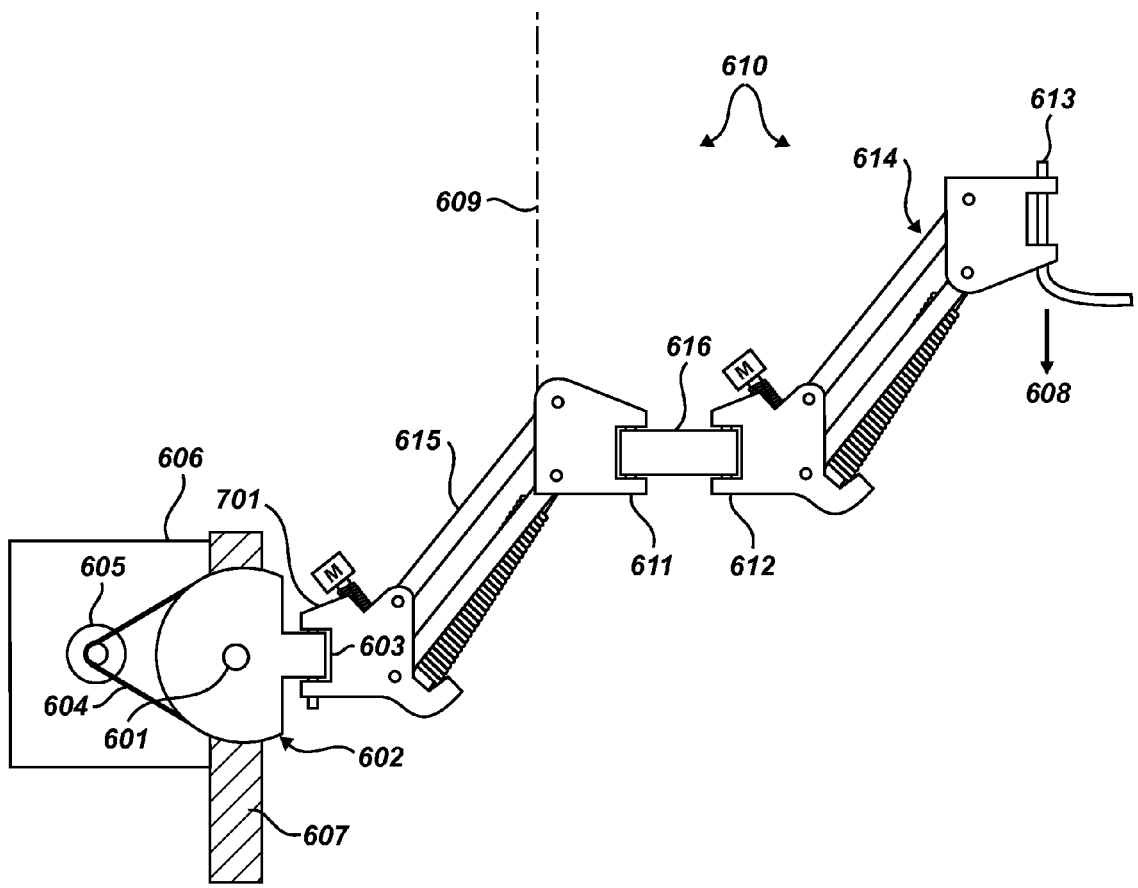
FIG. 6 shows a detail of the motorized rotatable arm mounting assembly that adjustably redirects the net force in vectors that may be non-parallel to that of gravity.

FIG. 6 shows a detail of the motorized rotating arm mounting assembly 600 that (as shown and/or described in FIG. 3), adjustably directs the net arm force 608 in vectors that may be non-parallel to that of gravity 609. Servo-motor 605 may be controlled by foot pedals (not shown) or mechanical levers (not shown) operated by the medical practitioner. Primary hinge pin 603 is angularly fixed to partial sector gear 602 which pivots about axle 601, driven by motor 605 via belt 604 in order to alter the angle of hinge pin 603 (and thus that of the entire arm assembly 610) in order to bias net exerted force vector 608 in a direction non-parallel with that of gravity. As noted above in regard to FIG. 3, mounting assembly 600, pivoting on axle 601 may also operate in combination with an additional perpendicular adjustment axle (not shown) or may be replaced by other mechanically operated means for angular adjustment known in the art, such as a gimbal or a ball joint to provide either manual or motorized redirection of net force vector 310 or 608 to any desired axis non-parallel with that of gravity including those up to 90 degrees displaced therefrom. The effect of these adjustments will be to cause any or all of hinge pins 603, 611, 612, 613 to depart from vertical, thus biasing the associated hinged components of arm assembly 610 to swivel toward the vector of gravity. Depending on the previous angular relationship of arm segments 614 and 615, this bias might cause them to fold around hinge 616 in a desired direction to apply a lateral component to force vector 608.

Figure 7:
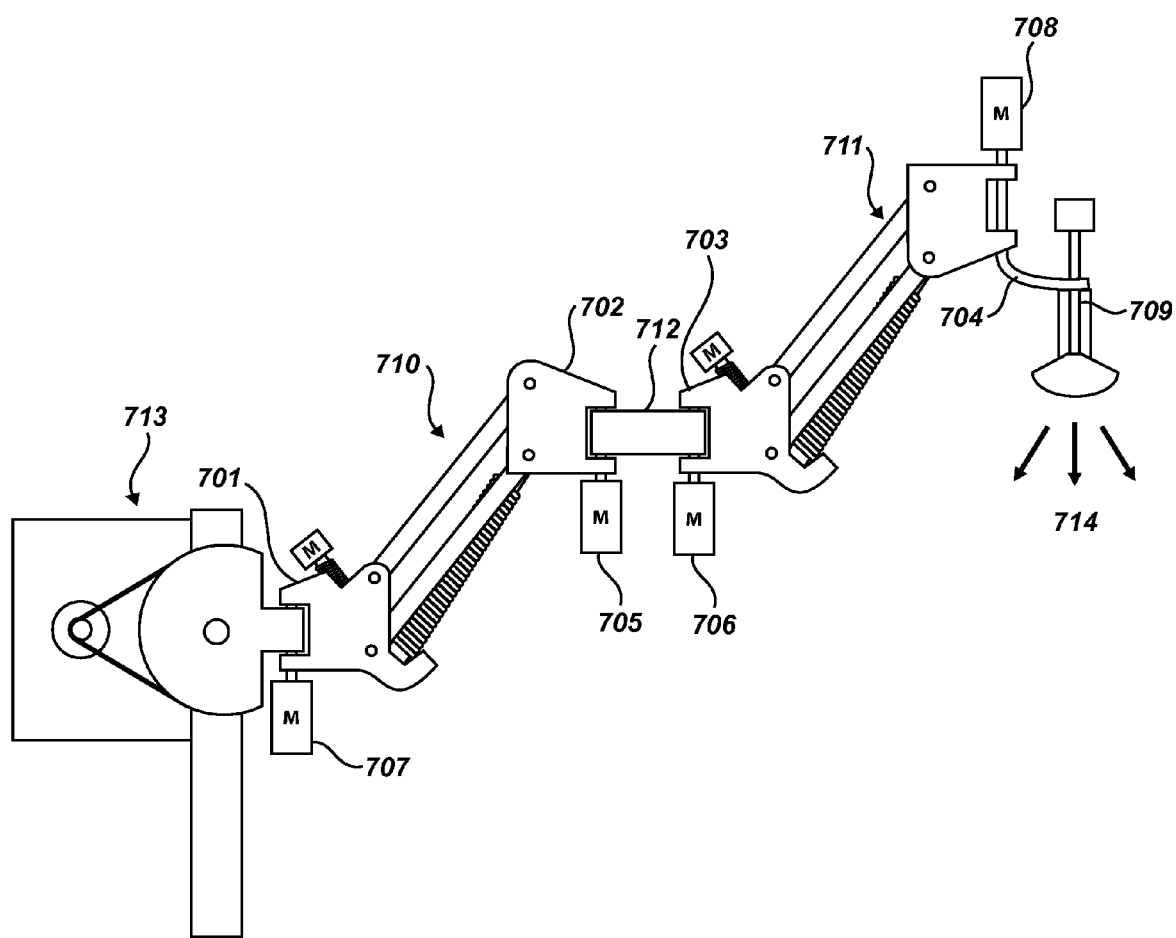
FIG. 7 shows the motorized biasing of the hinges that interconnect individual arm sections to each other and also to the mounting structure, in order to adjustably bias the net arm force in an additional collective vector that may be non-parallel to that of gravity.

FIG. 7 illustrates a third means of adjustment that can bias the individual hinge segments that interconnect the various sections of the arm assembly in order to selectably add a separate, and/or additional, lateral force. FIG. 7 is a perspective view showing the servo-motor-powered biasing of the hinges 701, 702, 703, 704 that interconnect individual arm sections 710, 711 to each other and also to the mounting structure 713, in order to additionally bias the net arm force 714 in vectors that may be non-parallel to that of gravity. The adjusting means shown, unlike the adjusting means described above in FIG. 6, provide that angle of the overall arm assembly 700, as determined by the angle of hinge pins 701, 702, 703, 704, is not further altered. Rather, its angular relationship to the mounting assembly 713 and/or the angular relationship of parallelograms 710, 711 to each other, are forcibly biased by motors 707, 705, 706, 708 to selected orientations around their respective hinges. This may additionally alter the net force vector 714 for the purposes of pressing payload 709 in a desired direction.

Figure 8:
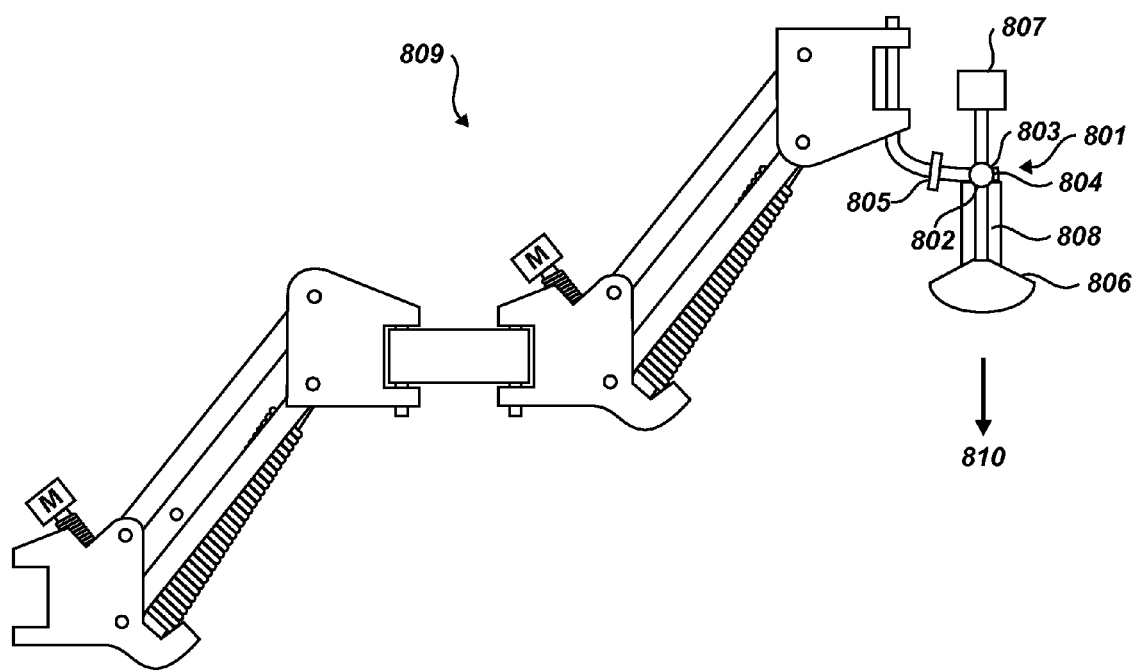
FIG. 8 shows perspective detail of the gimbaled three-axis sensors arranged to detect and transmit the ultrasonographer's intended vectors of force in three roughly perpendicular angles.

FIG. 8 shows detail of gimbaled three-axis, force-activated sensors 805, 804, 802, 803 arranged to detect and transmit the ultrasonographer's intended vectors of force (illustrated here as arrow 810) in three roughly perpendicular angles. (The wires from the sensors are not shown). These sensors, mechanically associated with the universal transducer mounting boot 808 in a conventional manner, permit the movement and hand pressure applied to the axis of the transducer 806 to be servo-amplified and steadied by the articulated arm 809 of the present invention. Transducer 806 and mounting boot 808 are mounted on gimbal assembly 801, counterbalanced by counterweight 807 which collectively form the payload 800 which is in gimbaled connection to arm assembly 809 such that it preferably has little or no angular bias of its own and may be held effortlessly by the ultrasonographer (not shown) at any angle. Additional (or other)adjustments to the forces applied by the articulated arm may still be effected by use of the foot pedals (not shown) or by simple mechanical leverage applied by the operator's foot directly to a treadle connected to an arm mounting pivot (not shown).

Use of the above detailed preferred embodiments, would require only minimal retraining of medical professionals and no alterations to existing ultrasound equipment.

While the invention has been described by illustrative embodiments, additional advantages and modifications will occur to those skilled in the art. Therefore, the invention in its broader aspects is not limited to specific details shown and described herein. Modifications, for example, to the materials, specific components and their layout, may be made without departing from the spirit and scope of the invention. Accordingly, it is intended that the invention not be limited to the specific illustrative embodiments, but be interpreted within the full spirit and scope of the appended claims and their equivalents.

What is claimed is:

1. A force-exerting device comprising:
a force-exerting arm having:
   a) a load arm pivotal about a load pivot and the load arm forming a first side of a force exerting structure; the load arm having a first end attached to the load pivot and the load arm having a second end attached to a payload;
   b) a first end block to which the load arm is attached at the load pivot and;
   c) a resilient member forming a second side of the force exerting structure, the resilient member having a first end attached to the second end of the load arm and the resilient member having a second end adjustably attached to a lead screw, the lead screw being offset from vertical and being secured to the first end block;
   d) a line between the load pivot and resilient member second end forming a third side of the force exerting structure;
   e) the lead screw crossing a virtual line coincident with the plumb line, the plumb line extending through the load pivot;
   f) the resilient member second end adjustable along a length of the lead screw from a position above the level of the load pivot to a position below the level of the load pivot;
   g) a mounting sructure;
   h) the force-exerting arm secured to the mounting structure; and
   i) the mounting structure containing a pivoting single-axis connection assembly connecting the force-exerting arm to a support structure, the single-axis connection assembly pivotal about a horizontal axis to alter the angle of the virtual line so it is no longer coincident with the plumb line.

2. The force-exerting device of claim 1 further comprising:
a second parallelogram structure pivotally attached to the first parallelogram structure by a hinge having a first hinge pin and a second hinge pin; and
a motor functionally attached to the first double axis hinge pin to bias the first double axis hinge pin hinge thereby producing a lateral force on the payload.

3. The force-exerting device of claim 1 wherein the single-axis connection assembly comprises:
a sector gear functionally connected to the force-exerting arm and the support structure by a belt to adjust the angle of the virtual line, thereby adding a lateral component to a gravity vector to which the payload is subjected.

4. A force-exerting device comprising:
a force-exerting arm having:
   a) a load arm pivotal about a load pivot and the load arm forming a first side of a force exerting structure; the load arm having a first end attached to the load pivot and the load arm having a second end attached to a payload;
   b) a first end block to which the load arm is attached at the load pivot and;
   c) a resilient member forming a second side of the force exerting structure, the resilient member having a first end attached to the second end of the load arm and the resilient member having a second end adjustably attached to a lead screw, the lead screw being offset from vertical and being secured to the first end block;
   d) a line between the load pivot and resilient member second end forming a third side of the force exerting structure;
   e) the lead screw crossing a virtual line coincident with the plumb line, the plumb line extending through the load pivot;
   f) the resilient member second end adjustable along a length of the lead screw from a position above the level of the load pivot to a position below the level of the load pivot;

g) a gimbal assembly wherein the load arm second end is attached to the payload by the gimbal assembly; and h) a plurality of force-activated sensors functionally arranged to detect and transmit the direction of a user's intended force on the payload to one or more motors causing the one or more motors to amplify the magnitude of the user's force in the intended direction to reduce the exerted force required by the user on the payload in any direction.

5. The force exerting device of claim 4 further comprising:
a second parallelogram structure pivotally attached to the first parallelogram structure by a hinge having a first hinge pin and a second hinge pin.

6. The force exerting device of claim 5 with a motor functionally attached to the first hinge pin to bias the hinge thereby producing a lateral force on the payload.

7. A force-exerting arm having:
 a) a load arm pivotal about a load pivot and the load arm forming a first side of a force exerting structure; the load arm having a first end attached to the load pivot and the load arm having a second end attached to a payload;
 b) a first end block to which the load arm is attached at the load pivot and;
 c) a resilient member forming a second side of the force exerting structure, the resilient member having a first end attached to the second end of the load arm and the resilient member having a second end adjustably attached to a lead screw, the lead screw being offset from vertical and being secured to the first end block;
 d) a line between the load pivot and resilient member second end forming a third side of the force exerting structure;
 e) the lead screw crossing a virtual line coincident with the plumb line, the plumb line extending through the load pivot;
 f) the resilient member second end adjustable along a length of the lead screw from a position above the level of the load pivot to a position below the level of the load pivot;
 g) wherein the force-exerting structure is contained in a first parallelogram structure comprising:
 h) the first end block having the load pivot and an upper pivot;
 i) a second end block having a lower pivot and an upper pivot;
 j) the load arm extending between the first end block load pivot and the second end block lower pivot;
 k) a linking arm pivotally attached to the first end block and the second end block, extending between the first end block upper pivot and the second end block upper pivot;
 l) the second end block pivotally attached to a mounting support by a hinge pin;
 m) a motor functionally attached to the mounting support hinge pin to bias the end block about the mounting support hinge pin thereby producing a lateral force on the payload;
 n) a second parallelogram structure pivotally attached to the first parallelogram structure by a double axis hinge having a first hinge pin and a second hinge pin;
 o) a motor functionally attached to the first double axis hinge pin to bias the first double axis hinge pin hinge thereby producing a lateral force on the payload;
 p) a motor functionally attached to the second double axis hinge pin to bias the second double axis hinge pin hinge thereby producing a lateral force on the payload;
 q) a mounting structure;
 r) the force-exerting arm secured to the mounting structure;
 s) the mounting structure containing a pivoting single-axis connection assembly connecting the force-exerting arm to a support structure, the single-axis connection assembly pivotal about a horizontal axis to alter the angle of the virtual line so it is no longer coincident with the plumb line;
 t) a gimbal assembly wherein the load arm second end is attached to the payload by the gimbal assembly; and
 u) a plurality of force-activated sensors functionally arranged to detect and transmit the direction of a user's intended force on the payload to one or more motors causing the one or more motors to amplify the magnitude of the user's force in the intended direction.

8. A force-exerting arm having:
 a) a load arm pivotal about a load pivot and the load arm forming a first side of a force exerting structure; the load arm having a first end attached to the load pivot and the load arm having a second end attached to a payload;
 b) a first end block to which the load arm is attached at the load pivot and;
 c) a resilient member forming a second side of the force exerting structure, the resilient member having a first end attached to the second end of the load arm and the resilient member having a second end adjustably attached to a lead screw, the lead screw being offset from vertical and being secured to the first end block;
 d) a line between the load pivot and resilient member second end forming a third side of the force exerting structure;
 e) the lead screw crossing a virtual line coincident with the plumb line, the plumb line extending through the load pivot;
 f) the resilient member second end adjustable along a length of the lead screw from a position above the level of the load pivot to a position below the level of the load pivot;
wherein the force-exerting structure is contained in a first parallelogram structure comprising:
 a) the first end block having the load pivot and an upper pivot;
 b) a second end block having a lower pivot and an upper pivot;
 c) the load arm extending between the first end block load pivot and the second end block lower pivot;
 d) a linking arm pivotally attached to the first end block and the second end block, extending between the first end block upper pivot and the second end block upper pivot;
 e) the second end block pivotally attached to a mounting support by a hinge pin;
 f) a motor functionally attached to the mounting support hinge pin to bias the end block about the mounting support hinge pin thereby producing a lateral force on the payload;
 g) a second parallelogram structure pivotally attached to the first parallelogram structure by a hinge having a hinge pin;
 h) a motor functionally attached to the first hinge pin to bias the hinge thereby producing a lateral force on the payload;
 i) a mounting structure;
 j) the force-exerting arm secured to the mounting structure;
 k) the mounting structure containing a pivoting single-axis connection assembly connecting the force-exerting arm to a support structure, the single-axis connection assembly pivotal about a horizontal axis to alter the angle of the virtual line so it is no longer coincident with the plumb line;

l) a gimbal assembly wherein the load arm second end is attached to the payload by the gimbal assembly; and m) a plurality of force-activated sensors functionally arranged to detect and transmit the direction of a user's intended force on the payload to one or more motors causing the one or more motors to amplify the magnitude of the user's force in the intended direction.

* * * * *